United States Patent [19]

Steiner et al.

[11] Patent Number: 4,745,111
[45] Date of Patent: May 17, 1988

[54] ANTI-ANXIETY, ANTI-AGITATION, AND ANTI-SLEEPLESS STATES 4-SUBSTITUTED 10-CYANOMETHYLENETHIENO-[4,3-E]BENZOAZEPINE DERIVATIVES, COMPOSITIONS, AND METHODS OF USE THEREFOR

[75] Inventors: Gerd Steiner, Kirchheim; Hans-Juergen Teschendorf, Dudenhofen; Liliane Unger, Ludwigshafen, all of Fed. Rep. of Germany

[73] Assignee: BASF Aktiengesellschaft, Ludwigshafen, Fed. Rep. of Germany

[21] Appl. No.: 883,628

[22] Filed: Jul. 9, 1986

[30] Foreign Application Priority Data

Jul. 11, 1985 [DE] Fed. Rep. of Germany ....... 3524744

[51] Int. Cl.$^4$ .................... A61K 31/55; C07D 223/14; C07D 223/16
[52] U.S. Cl. .................... 514/215; 514/217; 540/586
[58] Field of Search ................ 540/586; 514/215, 217

[56] References Cited

U.S. PATENT DOCUMENTS 3,959,282  5/1976  Hunziker et al. ................... 540/586
4,362,727 12/1982  Steiner et al. ....................... 540/586

FOREIGN PATENT DOCUMENTS 0001401  4/1979  European Pat. Off. ............ 540/586

OTHER PUBLICATIONS

Schmutz, J., "Neuroleptic Piperazinyl-Dibenzo-Azepines", Arzneim.-Forsch. (Drug Res.) 25, Nr. 5(1975) pp. 712-720.

Primary Examiner—Henry R. Jiles
Assistant Examiner—J. G. Mullins
Attorney, Agent, or Firm—Keil & Weinkauf

[57] ABSTRACT

Compounds of the formula

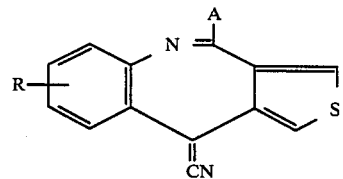

where R and A have the meanings given in the description, and their use in the treatment of disorders are described.

14 Claims, No Drawings

ANTI-ANXIETY, ANTI-AGITATION, AND ANTI-SLEEPLESS STATES 4-SUBSTITUTED 10-CYANOMETHYLENETHIENO-[4,3-E]BENZOAZEPINE DERIVATIVES, COMPOSITIONS, AND METHODS OF USE THEREFOR

The present invention relates to 10-cyanomethylenethieno[4,3-e]benzoazepines which are substituted in the 4-position, processes for their preparation, and their use as drugs, such as sedatives, hypnotics, tranquilizers, muscle relaxants, neuroleptics or antiparkinson agents.

It is known that tricyclic ring systems possessing a dibenzo structure with respect to a central 7-membered heterocyclic ring which may have a basic side radical, e.g. an N-methylpiperazine radical, may exhibit a neuroleptic action. Examples of such tricyclic compounds are N-methylpiperazine derivatives of dibenzo[b,e][1,4-]diazepines (clozapine), dibenzo[b,f][1,4]thiazepines (clotiapine), dibenzo[b,f][1,4]oxazepines (loxapine) and morphanthridines (perlapine), as described in, for example, the summary by J. Schmutz in Arzneimittelforschung 25 (1975), 712-720.

German Laid-Open Applications Nos. DOS 2,918,778 and DOS 3,037,971 describe, respectively, 6-substituted 11-alkylenemorphanthridines and 5-substituted 9-cyanomethylenedithieno[3,4-b:4', 3'-e]azepines possessing useful pharmacological properties.

We have found that 4-substituted 10-cyanomethylenethieno[4,3-e]benzoazepines of the formula I

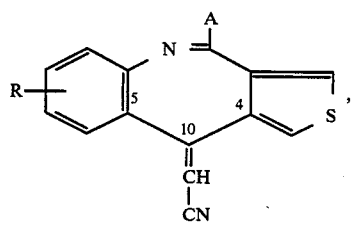

where R is hydrogen, halogen, alkyl of 1 to 3 carbon atoms, trifluoromethyl or alkoxy of 1 to 3 carbon atoms and A is an amino radical $-NR^1R^2$, in which $R^1$ and $R^2$, together with the nitrogen atom to which they are bonded, form a saturated 5-membered, 6-membered or 7-membered ring which may contain nitrogen or oxygen as a further heteroatom, and any additional nitrogen atom present is unsubstituted or substituted by alkyl of 1 to 3 carbon atoms, hydroxyalkyl of 2 or 3 carbon atoms, alkoxyalkyl where the alkyl and alkoxy radicals are each of 1 to 3 carbon atoms, cycloalkyl or cycloalkylmethyl, each of which has 3 to 7 carbon atoms in the cycloalkyl ring, or alkynyl of 2 to 5 carbon atoms, and may additionally be substituted by oxygen in the form of an N-oxide, or A is an amino radical $-NHR^3$ where $R^3$ is aminoalkyl of 2 to 7 carbon atoms and the amine nitrogen is unsubstituted or substituted by lower alkyl of 1 to 5 carbon atoms or forms part of a saturated 5-membered, 6-membered or 7-membered ring which may contain nitrogen or oxygen as a further heteroatom, and any nitrogen atom present may be substituted by lower alkyl of 1 to 3 carbon atoms or hydroxyalkyl of 2 or 3 carbon atoms, and their physiologically tolerated addition salts with acids, possess useful pharmacological properties.

Particularly suitable radicals R are hydrogen, fluorine, chlorine, methyl, trifluoromethyl and methoxy.

Preferred amine radicals $-NR^1R^2$ for A are piperazinyl, homopiperazinyl, piperidinyl and morpholinyl.

Particularly preferred radicals $-NR^1R^2$ are 4-methylpiperazinyl, 4-methyl-4-oxypiperazinyl, 4-ethylpiperazinyl and N-methylhomopiperazinyl.

In the amine radical $-NHR^3$, $R^3$ is, in particular, 2-dimethylaminoethyl or 2-piperidin-1-ylethyl.

It should be pointed out that the novel compounds of the formula I occur as cis and trans isomers Ia and b

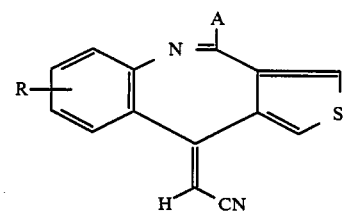

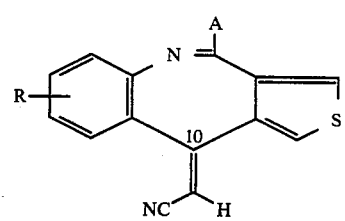

The cis/trans isomers can be separated by, for example, fractional crystallization or column chromatography.

The individual isomers are identified by, for example, X-ray structural analysis, as can be seen from the Examples.

On the basis of the meanings stated above, the following compounds are particularly preferred and effective: cis,trans-10-cyanomethylene-4-(4-methylpiperazin-1-yl)-thieno[4,3-e]benzoazepine, cis-10-cyanomethylene-4-(4-methylpiperazin-1-yl)-thieno 4,3-e]-benzoazepine, trans-10-cyanomethylene-4-(4-methylpiperazin-1-yl)-thieno-[4,3-e]benzoazepine, cis,trans-7-chloro-10-cyanomethylene-(4-methylpiperazin-1-yl)-thieno[4,3-e]benzoazepine, cis-7- chloro-10-cyanomethylene-4-(4-methylpiperazin-1-yl)-thieno-[4,3-e]benzoazepine, trans-7-chloro-10-cyanomethylene-4-(4-methylpiperazin-1-yl)-thieno[4,3-e]benzoazepine, cis, trans-7-fluoro-10-cyanomethylene-4-(4-methylpiperazin-1- yl)-thieno]4,3-e]benzoazepine, cis,trans-7-methyl-10cyanomethylene-4-(4-methylpiperazin-1-yl)-thieno[4,3-e]benzoazepine, cis,trans-7-trifluoromethyl-10-cyanomethylene-4-(4-methylpiperazin-1-yl)-thieno[4,3-e]benzoazepine, cis, trans-7-methoxy-10-cyanomethylene-4-(4-methylpiperazin-1- yl)-thieno[4,3-e]benzoazepine and cis,trans-10-cyanomethylene-4-piperazin-1-yl)-thieno[4,3-e]benzoazepine.

As shown in the illustrative examples, separation into the cis and trans isomers can be carried out in individual cases without a great deal of expense.

The novel compounds of the formula I are prepared by a method in which a compound of the formula II

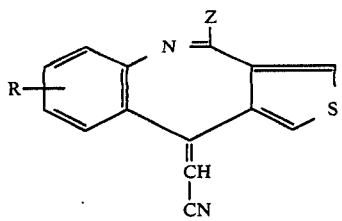

where R has the stated meanings and Z is a nucleofugic leaving group, is reacted with a nucleophile AH, where A has the meanings stated for formula I, the product is, if required, separated into the pure cis and trans isomers and/or, if desired, the resulting compound is converted to the N-oxide and/or to an addition salt with a physiologically tolerated acid.

Suitable nucleofugic leaving groups Z are halogen atoms, in particular bromine or chlorine.

The reaction is advantageously carried out in an excess of the amine AH used, which serves simultaneously as the solvent and, where relevant, as an acid acceptor. If necessary, the reaction can be carried out in the presence of an inert solvent, such as a saturated cyclic ether, in particular tetrahydrofuran or dioxane, benzene or a benzene hydrocarbon, such as toluene, xylene, mesitylene or decahydronaphthalene, or an aprotic polar solvent, such as dimethylformamide. If only 1 equivalent of the amine AH is used, 1 equivalent of an inert base, e.g. triethylamine, must also be added.

The reaction is carried out as a rule at from 80° to 150° C. and is generally complete in the course of from 3 to 10 hours. It may be advantageous to exclude atmospheric oxygen and carry out the process under an inert gas, e.g. nitrogen.

In the reactions, the nucleophile AH is advantageously used in not less than a 2-fold to 20-fold molar excess.

Conversion of a compound of the formula I to the N-oxide is carried out in a conventional manner, advantageously with aqueous hydrogen peroxide (30% by weight) in ethanolic solution. Conversion to an addition salt with a physiologically tolerated acid is also effected in a conventional manner.

The starting compounds of the formula II are obtained by a method in which a 10-cyanomethylene-thieno[4,3-e]benzo-4,5-dihydroazepin-4-one of the formula III

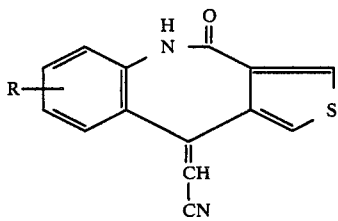

where R has the meanings stated for the formula II, is refluxed for from 3 to 5 hours with an excess of a halogenating agent such as phosphorus oxychloride in the presence of a solvent and of a catalytic amount of N,N-dimethylaniline, the excess phosphorus oxychloride is distilled off, the mixture is worked up in an aqueous two-phase system and the resulting iminochloride is then isolated by extraction with a chlorohydrocarbon such as methylene chloride.

The novel 10-cyanomethylenethieno[4,3-e]benzo-4,5-dihydroazepin-4-one of the formula III, where R has the meanings stated for formula I, is prepared by carbonyl olefination, by subjecting a thieno[4,3-e]benzo-4,5-dihydroazepin-4,10-dione of the formula IV

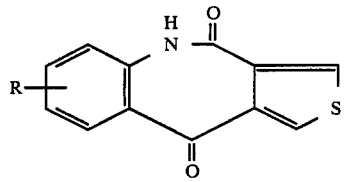

to a Wittig-Horner reaction with a phosphonate of the formula Va

where R is alkyl of 1 to 3 carbon atoms, in an inert solvent, particularly preferably dimethylformamide, in the presence of a one mole equivalent of a base, preferably a sodium alcoholate, sodium hydride or sodium amide, and at from 20° to 80° C., or to a classical Wittig reaction with a phosphonium salt of the formula Vb

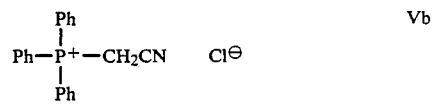

where Ph is phenyl, in an aprotic organic solvent, in particular a saturated aliphatic or saturated cyclic ether, such as diethyl ether, tetrahydrofuran or dioxane, or preferably in dimethylformamide, in the presence of 1 mole equivalent of a base, in particular sodium ethylate or sodium amide, or of an organometallic compound, such as butyllithium, at from 20° to 100° C.

The novel thieno[4,3-e]benzo-4,5-dihydroazepin-4,10-dione of the formula IV, where R has the meanings stated for formula I, is prepared by a Friedel-Crafts cyclization reaction, by converting a thiophene-3,4-dicarboxylic acid benzamide of the formula VI

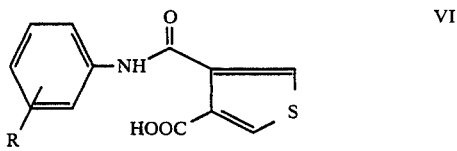

with N-hydroxysuccinimide, in the presence of one mole equivalent of dicyclohexylcarbodiimide, to an activated ester of the formula VII

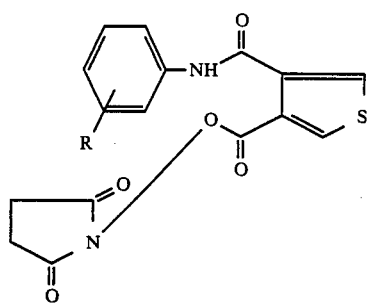

and then subjecting this to a Friedel-Crafts cyclization reaction in the presence of a 5-fold to 8-fold excess of aluminum chloride in a dipolar aprotic solvent, such as dimethylformamide, at from 50° to 120° C. for from 1 to 3 hours.

The first reaction (VI→VII) is carried out in an inert organic solvent, e.g. tetrahydrofuran, and is complete in the course of from 1 to 3 hours at room temperature. The precipitated urea is filtered off under suction, and the activated ester of the formula VII is isolated.

The thiophene-3,4-dicarboxylic acid benzamide of the formula VI is obtained in a simple manner by reacting thiophene-3,4-dicarboxylic anhydride with the corresponding aniline in tetrahydrofuran at room temperature for from 1 to 5 hours.

The novel compounds of the formula I are obtained, as a rule, in the form of yellowish or yellow crystals, and can be purified by recrystallization from a conventional organic solvent, preferably from a lower alcohol, such as ethanol, or by column chromatography.

If necessary, separation into the individual cis and trans isomers can be effected by fractional crystallization in a chlorohydrocarbon, preferably methylene chloride, a lower monohydric alcohol, preferably methanol or ethanol, or a saturated cycloaliphatic hydrocarbon, preferably cyclohexane, or by column chromatography, in particular in methylene chloride and methanol in a volume ratio of from 99:1 to 85:15.

The free substituted 10-cyanomethylenethieno[4,3-e]benzoazepines of the formula I can be converted in a conventional manner to an addition salt with a pharmacologically acceptable acid, preferably by adding one equivalent of the appropriate acid to a solution. Examples of pharmaceutically acceptable acids are hydrochloric acid, phosphoric acid, sulfuric acid, methanesulfonic acid, amidosulfonic acid, maleic acid, fumaric acid, oxalic acid, tartaric acid and citric acid.

In pharmacological experiments, the compounds according to the invention exhibit useful properties. In view of their sedative/muscle relaxing, antimonaminergic and central-anticholinergic action, they can be used as sedatives/hypnotics, minor and major tranquilizers and antiparkinson agents. They are therefore useful for the treatment of central nervous disturbances, in particular agitation and anxiety states, sleeplessness, endogenous and exogenous psychoses and Parkinson's disease.

A compound according to the invention may exhibit several of the stated types of action. An individual isomer (after isomer separation) may preferentially exhibit one particular action.

The following methods were used to characterize the actions.

1. Sedative action

The substances are administered orally to 4–8 groups of female NMRI mice, each group comprising 3 mice. The orientation hypermotility induced by a new environment was determined photoelectrically 30 minutes after administration of the substances, over a period of 30 minutes.

The $ED_{50}\%$, i.e. the dose which produces a 50% reduction in orientation hypermotility compared to placebo-treated control animals, is determined.

2. Apomorphine antagonistic action (Antidopaminergic action)

In mice kept in a suitable environment (e.g. a wire-mesh cage), apomorphine (1.21 mg/kg, administered subcutaneously) leads to increased climbing. The animals are observed for 30 minutes after administration of apomorphine, and the climbing is quantified every 2 minutes with the aid of a score. The test substances are administered perorally 60 minutes after administration of apomorphine. The $ED_{50}\%$ is calculated as the dose which reduces the scores by 50% compared with a control group.

3. L-5-HTP antagonism (Serotonin antagonism)

In the rat (316 mg/kg, administered intraperitoneally), L-5-hydroxytryptamine (L-5HTP), a prodrug for serotonin, leads to signs of agitation, such as shaking of the head, tremors and movements of the front feet. The animals are observed for 1 hour after administration of L-5HTP, and the symptoms occurring are quantified every 10 minutes with the aid of a score. The test substances are administered perorally 1 hour before L-5HTP. The $ED_{50}\%$ is calculated as the dose which produces on average a 50% reduction in the scores observed for a control group.

4. Anticholinergic action

A lethal dose (0.825 mg/kg) of physostigmin is administered subcutaneously to groups of 10 female NMRI mice. The test substances are administered orally 30 minutes before administration of physostigmin. The $ED_{50}\%$ is determined as the dose of substance which protects 50% of the animals from death due to physostigmin.

The results are summarized in the Table.

TABLE

| Example | Sedative action in the mouse $ED_{50}\%$ mg/kg p.o. | Antimonaminergic action | | Anticholinergic action Mouse $ED_{50}\%$ mg/kg p.o. |
|---|---|---|---|---|
| | | Apomorphine Mouse $ED_{50}\%$, mg/kg p.o. | L-5HTP antagonism Rat | |
| 1 | 0.89 | 1.7 | 0.77 | 15.8 |
| 1 (cis) | 0.35 | 1.0 | 1.0 | >10 |
| 1 (trans) | 5.1 | 10.9 | 33 | 5.2 |
| 9 | 0.81 | 1.0 | | >10 |
| 4 | 3.27 | ~2.0 | 1.0 | ~21 |
| 3 | 0.89 | ~2.0 | 0.8 | >21.5 |
| 16 | ~3.0 | | 1.0 | >10 |
| 5 | 3.75 | ~2.1 | 1.4 | >21.5 |
| Clozapine | 3.8 | 11.3 | 6.3 | 14.1 |

In these experiments, in which sedatives, minor or major tranquilizers and central anticholinergics display typical actions, the majority of the novel compounds exhibit good effects. The sedative and antimonaminergic action of the comparative substance is always reached and is generally surpassed by a substantial margin (up to 10 times). The anticholinergic action is less pronounced for the majority of the compounds, which, because of anticholinergic side effects, is advantageous in clinical use.

Separation of the isomers shows that the sedative and antimonaminergic action is displayed preferentially by the cis isomer (Example 1), the anticholinergic action being greatly reduced. In the trans isomer (Example 1) on the other hand, the anticholinergic action predominates, in conjunction with a fairly weak sedative and antimonaminergic action. The anticholinergic action is also stronger than that of the comparative substances.

The present invention accordingly also relates to a therapeutic agent which contains a compound of the formula I or its pharmacologically acceptable acid addition salt as an active compound, in addition to conventional carriers and diluents, and the use of the novel compounds in the treatment of disorders.

The compounds according to the invention can be administered in a conventional manner, orally, parenterally, intravenously or intramuscularly.

The dosage depends on the age, condition and weight of the patient and on the route of administration. As a rule, the daily dose of active compound is from about 1 to 20 mg per kg of body weight in the case of oral administration, and from 0.1 to 2 mg per kg of body weight for parenteral administration.

The novel compounds may be employed in the conventional solid or liquid pharmaceutical forms, such as tablets, film tablets, capsules, powders, granules, coated tablets, suppositories, solutions, ointments, creams or sprays. These are prepared in a conventional manner, and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, retarding agents, antioxidants and/or propellants (cf. H. Sucker et al.: Pharmazeutische Technologie, Thieme-Verlag, Stuttgart, 1978). The administration forms thus obtained usually contain from 0.1 to 99% by weight of the active compound.

The Examples which follow illustrate the invention.

EXAMPLE 1

A. Preparation of the starting materials a) Thiophene-3,4-dicarboxylic acid benzamide 10.9 g (117 millimoles) of aniline in 20 ml of toluene were added dropwise to 18.0 g (117 millimoles) of thiophene-3,4-dicarboxylic anhydride in 200 ml of toluene at room temperature, while stirring thoroughly. Stirring was continued for from 2 to 3 hours, after which the dense precipitate was filtered off under suction and washed thoroughly with toluene, and the solid was dried first in the air and subsequently under reduced pressure to give 28 g (98%) of a product of melting point 161°–163° C.

(b) 4,5-Dihydrothieno[4,3-e]benzoazepine-4,10-dione 17.5 g (71 millimoles) of thiophene-3,4-dicarboxylic acid benzamide were dissolved in 300 ml of tetrahydrofuran, and 8.2 g (71 millimoles) of N-hydroxysuccinimide and 14.7 g (71 millimoles) of N,N'-dicyclohexylcarbodiimide were added to the thoroughly stirred solution. The reaction product was stirred for a further 2 hours at room temperature, the precipitated urea was filtered off under suction and washed with a little tetrahydrofuran, and the filtrate was evaporated to dryness. The residue was introduced a little at a time into a melt consisting of 70 g (526 millimoles) of $AlCl_3$, with 10.5 ml of dimethylformamide at an internal temperature of 90° C. and with thorough stirring. The reaction mixture was kept at 90° C. for a further 2 hours, poured while still hot onto ice, acidified with HCl and stirred for some time, and the pale brown solid was then filtered off under suction. The product was washed with $H_2O$ and then dried in the air. 15.3 g (94%) of a product which was sufficiently pure for further reaction were obtained.

(c) cis,trans-10-Cyanomethylene-4,5-dihydrothieno[4,3-e]benzoazepin-4-one (cis/trans isomer mixture)

To prepare this product, carbonylolefination of 4,5-dihydrothieno[4,3-e]benzoazepin-4,10-dione was carried out by means of the Wittig-Horner reaction (a) or the classical Wittig synthesis (b):

(a) 8.8 g (38.5 millimoles) of 4,5-dihydrothieno[4,3-e]benzoazepin-4,10-dione were dissolved in 70 ml of dimethylformamide, with heating, and the mixture was stirred under nitrogen. 8.0 g (45 millimoles) of diethyl cyanomethylphosphonate and 8.1 g (45 millimoles) of 30% strength sodium methylate dissolved in 10 ml of dimethylformamide were then slowly added dropwise at the same time, the beginning of the Wittig reaction being indicated by an increase in color and in temperature. The reaction mixture was stirred for 12 hours at room temperature and then poured onto ice water, and the precipitated solid was filtered off under suction. The crude product was washed thoroughly with water, dried and recrystallized from ethanol to give 8.8 g (91%) of 10-cyanomethylene-4,5-dihydrothieno[4,3-e]benzoazepin-4-one in the form of colorless crystals of melting point >265° C.

(b) Triphenyl-cyanomethyl-phosphonium chloride in dimethylformamide was initially taken, 1 mole equivalent of a 30% strength sodium methylate solution was added dropwise or 1 mole equivalent of sodium hydride was introduced and finally 1 mole equivalent of a solution of 4,5-dihydrothieno[4,3-e]benzoazepin-4,10-dione in dimethylformamide was added. The reaction mixture was stirred for from 5 to 8 hours at from 50° to 80° C., after which it was poured onto ice water and extracted several times with methylene chloride. The organic phase was dried and evaporated down, and the crude product was recrystallized from ethanol to give colorless crystals of melting point >265° C., in a yield of 65%.

B. Preparation of the end product cis- and trans-10-cyanomethylene-4-(4-methylpiperazin-1-yl)-thieno[4,3-e]benzoazepine (a) 30 ml of phosphorus oxychloride and 1.0 ml of N,N-dimethylaniline were added to 11.0 g (44 millimoles) of 10-cyanomethylene-4,5-dihydrothieno[4,3-e]benzoazepin-4-one (cis/trans isomer mixture) in 100 ml of 1,1,2-trichloroethane, and the mixture was refluxed for 0.5 hour under a nitrogen atmosphere. When the excess phosphorus oxychloride and dimethylaniline had been completely distilled off under reduced pressure from an oil pump, the residue was partitioned between methylene chloride and water, the aqueous phase was extracted twice with methylene chloride and the combined organic phases were washed thoroughly with dilute HCl and water, dried and evaporated down to give 11.6 g (98%) of 4-chloro-10-cyanomethylene-thieno[4,3-e]benzoazepine, which was sufficiently pure for further reaction.

11.6 g (43 millimoles) of 4-chloro-10-cyanomethylenethieno[4,3-e]benzoazepine were dissolved in 70 ml of dimethylformamide, and 10 ml (90 millimoles) of N-methylpiperazine and 10 ml (75 millimoles) of triethylamine were added, a highly exothermic reaction taking place. The mixture was stirred for from 2 to 3 hours at 100° C. under nitrogen, the dark homogeneous reaction mixture was then cooled and poured onto ice water, the yellowish crude product 10-cyanomethylene-4-(4-methylpiperazin-1-yl)-thieno[4,3-e]benzoazepine, was filtered off under suction. The crude product was dried in a drying oven under reduced pressure and then recrystallized from ethanol with the addition of active carbon or purified by column chromatography (silica gel, mobile phase 95:5 methylene chloride/methanol). 11.6 g (81%) of yellowish 10-cyanomethylene4-(4-methylpiperazin-1-yl)-thieno[4,3-e]benzoazepine were obtained in the form of a cis/trans isomer mixture of melting point 90°-92° C.

(b) To separate the cis/trans isomers, the isomer mixture was fractionally recrystallized from ethanol. The first fraction isolated consisted of 3.1 g of yellow crystals, which were shown from the thin layer chromatogram (silica gel, mobile phase 85:15 toluene/methanol) to consist mainly of the nonpolar isomer a.

When the filtrate had been concentrated somewhat by evaporation, 2.9 g of product crystallized out slowly from the filtrate in the form of yellow crystals, which were shown from the thin layer chromatogram (silica gel, mobile phase 85:15 toluene/methanol) to consist mainly of the polar isomer b.

The cis and trans isomers were obtained in virtually pure form by subsequent crystallization of the enriched products a and b from ethanol.

X-ray structure analysis showed that a was the cis isomer and b the trans isomer of 10-cyanomethylene-4-(4-methylpiperazin-1-yl)-thieno[4,3-e]benzoazepine.

M.p.: cis isomer a 191°-193° C.; trans isomer b 220°-221° C.

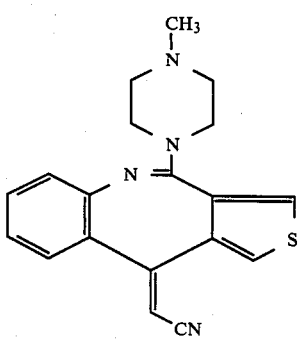
a

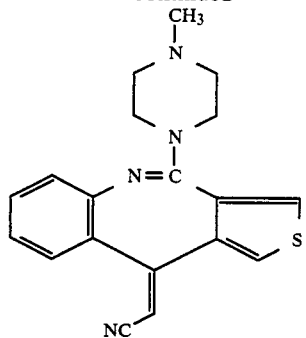
b

EXAMPLE 2 cis,trans-10-Cyanomethylene-4-(4-methyl-4-oxypiperazin-1-yl)-thieno[4,3-e]benzoazepine 2.8 g (8.4 millimoles) of cis,trans-10-cyanomethylene-4-(4-methylpiperazin-1-yl)-thieno[4,3-e]benzoazepine (cf. Example 1) were dissolved in 100 ml of hot ethanol, and 1.5 ml of 30% strength hydrogen peroxide were added. The mixture was refluxed for 5 hours, after which the excess hydrogen peroxide was destroyed with the aid of a small platinum sheet introduced into the reaction mixture, by refluxing for 2 hours. The reaction mixture was filtered, the filtrate was evaporated down and the resulting N-oxide was purified by column chromatography (silica gel, mobile phase 95:5 methylene chloride/methanol). 1.8 g (63%) of yellow crystals were isolated.

The substances below were obtained similarly to Examples 1 and 2, using the corresponding substituted amines:

3. cis,trans-7-chloro-10-cyanomethylene-4-(4-methylpiperazin-1-yl)-thieno[4,3-e]benzoazepine.
3a. cis-7-chloro-10-cyanomethylene-4-(4-methylpiperazin1-yl)-thieno[4,3-e]benzoazepine.
3b. trans-7-chloro-10-cyanomethylene-4-(4-methylpiper-azin-1-yl)-thieno[4,3-e]benzoazepine.
4. cis,trans-7-fluoro-10-cyanomethylene-4-(4-methylpiperazin-1-yl)-thieno[4,3-e]benzoazepine.
5. cis,trans-7-methyl-10-cyanomethylene-4-(4-methylpiperazin-1-yl)-thieno[4,3-e]benzoazepine.
6. cis,trans-7-trifluoromethyl-10-cyanomethylene-4-(4-methylpiperazin-1-yl)-thieno[4,3-e]benzoazepine.
7. cis,trans-7-methoxy-10-cyanomethylene-4-(4-methylpiperazin-1-yl)-thieno[4,3-e]benzoazepine.
8. cis,trans-10-cyanomethylene-4-(piperazin-1-yl)thieno[4,3-e]benzoazepine.
9. cis,trans-10-cyanomethylene-4-(4-ethylpiperazin-1-yl)-thieno[4,3-e]benzoazepine.
10. cis,trans-10-cyanomethylene-4-(N'-methylhomopiperazin-1-yl)-thieno[4,3-e]benzoazepine.
11. cis,trans-10-cyanomethylene-4-(2-piperidin-1-ylethylamino)-thieno[4,3-e]benzoazepine.
12. cis,trans-10-cyanomethylene-4-(2-dimethylaminoethylamino)-thieno[4,3-e]benzoazepine.
13. cis,trans-10-cyanomethylene-4-(4-cyclopropylpiperazin-1-yl)-thieno[4,3-e]benzoazepine.
14. cis,trans-10-cyanomethylene-4-(4-cyclopropylmethyl piperazin-1-yl)-thieno[4,3-e]benzoazepine.
15. cis,trans-10-cyanomethylene-4-(4-propin-2-yl piperazin-1-yl)-thieno[4,3-e]benzoazepine.
16. trans-6-chloro-10-cyanomethylene-4(4-methylpiperazin-1-yl)-thieno[4,3-e]benzoazepine.

EXAMPLE 19

A mixture having the following composition was pressed to give tablets in a conventional manner on a tableting machine:
40 mg of the substance of Example 1 (cis)
120 mg of corn starch
13.5 mg of gelatine
45 mg of lactose
2.25 mg of Aerosil ® (chemically pure silica in the form of submicroscopic particles)
6.75 mg of potato starch (as a 6% strength paste)

EXAMPLE 20

Coated tablets having the following composition were produced in a conventional manner:
20 mg of the substance of Example 1 (cis)
60 mg of core material
60 mg of sugar-coating material The core material consists of 9 parts of corn starch, 3 parts of lactose and 1 part of Luviskol ® VA 64 (60:40 vinylpyrrolidone/vinyl acetate copolymer, cf. Pharm. Ind. 1962, 586). The sugar-coating material consists of 5 parts of sucrose, 2 parts of corn starch, 2 parts of calcium carbonate and 1 part of talc. The coated tablets produced in this manner are then provided with a shell which is resistant to gastric juice.

EXAMPLE 21

10 g of the substance of Example 1 (cis) are dissolved in 5000 ml of water, with the addition of NaCl, and the solution is brought to pH 6.0 with 0.1N NaOH so that a solution which is isotonic with blood is formed. 5 ml portions of this solution are introduced into ampules and sterilized.

We claim:

1. A 4-substituted 10-cyanomethylenethieno[4,3-]-benzoazepine of the formula I

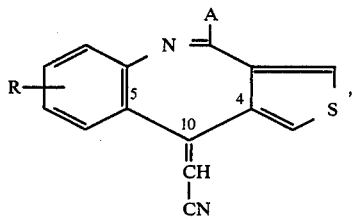

where R is hydrogen, halogen, alkyl of 1 to 3 carbon atoms, trifluoromethyl or alkoxy of 1 to 3 carbon atoms and A is an amino radical —NR$^1$R$^2$, in which R$^1$ and R$^2$, together with the nitrogen atom to which they are bonded, form a saturated 5-membered, 6-membered or 7-membered ring which may contain nitrogen or oxygen as a further heteroatom, and any additional nitrogen atom present is unsubstituted or substituted by alkyl of 1 to 3 carbon atoms, hydroxyalkyl of 2 or 3 carbon atoms, alkoxyalkyl where the alkyl and alkoxy radicals are each of 1 to 3 carbon atoms, cycloalkyl or cycloalkylmethyl, each of which has 3 to 7 carbon atoms in the cycloalkyl ring, or alkynyl of 2 to 5 carbon atoms, and may additionally be substituted by oxygen in the form of an N-oxide, or A is, piperidinyl, piperazinyl or homopiperazinyl, wherein any ring nitrogen atom may be substituted by hydrogen, methyl, ethyl, β-hydroxyethyl, cyclopropyl or propynyl and/or may be present in the form of the n-oxide, and its physiologically tolerated additional salts with acids.

2. A compound of the formula I as claimed in claim 1, wherein R is hydrogen, chlorine or fluorine.

3. cis,trans-10-Cyanomethylene-4-(4-methylpiperazin-1-yl)-thieno[4,3-e]benzoazepine.

4. cis-10-Cyanomethylene-4-(4-methylpiperazin-1-yl)thieno[4,3-e]benzoazepine.

5. trans-10-Cyanomethylene-4-(4-methylpiperazin-1-yl)thieno[4,3-e]benzoazepine.

6. cis,trans-7-Chloro-10-cyanomethylene-(4-methylpiperazin-1-yl)-thieno[4,3-e]benzoazepine.

7. cis-7-Chloro-10-cyanomethylene-4-(4-methylpiperazin--yl)-thieno[4,3-e]benzoazepine.

8. trans-7-Chloro-10-cyanomethylene-4-(4-methylpiperazin-1-yl)-thieno[4,3-e]benzoazepine.

9. cis,trans-7-Fluoro-10-cyanomethylene-4-(4-methylpiperazin-1-yl)-thieno[4,3-e]benzoazepine.

10. A benzoazepine of the formula I as defined in claim 1, wherein R is hydrogen, fluorine, chlorine, methyl, CF$_3$ or methoxy and A is a radical selected from the group consisting of piperazinyl, homopiperazinyl, 4-methylpiperazinyl, N-methylhomopiperazinyl, 4-methyl-4-oxypiperazinyl and 4-ethylpiperazinyl.

11. A pharmaceutical composition for treating agitation, anxiety and sleepless states, comprising a pharmaceutically acceptable carrier and a compound according to claim 1 in amount effective to relieve agitation, anxiety or sleepless states.

12. A therapeutic composition as defined in claim 10, wherein a compound according to claim 10 is used as the active compound.

13. The method of treating agitation, anxiety and sleepless states, in a patient suffering therefrom, which comprises administering to the patient an amount of a compound according to claim 1, effective to relieve the agitation, anxiety, or sleeplessness.

14. The method of claim 13, wherein a compound according to claim 10 is used as the active agent.

* * * * *